United States Patent [19]
Bishai et al.

[11] Patent Number: 5,824,546
[45] Date of Patent: Oct. 20, 1998

[54] REGULATION OF A SIGMA FACTOR FROM MYCOBACTERIUM TUBERCULOSIS

[75] Inventors: William R. Bishai, Baltimore, Md.; James DeMaio, Tacoma, Wash.

[73] Assignee: The Johns Hopkins University, Baltimore, Md.

[21] Appl. No.: 622,352

[22] Filed: Mar. 27, 1996

[51] Int. Cl.$^6$ .............................. C12N 5/10; C12N 1/00; C12N 15/31; C12N 15/63

[52] U.S. Cl. .......................... 435/325; 435/410; 435/243; 435/320.1; 536/23.7

[58] Field of Search ........................ 536/23.7; 435/325, 435/410, 243, 320.1

[56] References Cited

PUBLICATIONS

Smith et al., "Epidemioilogy of Tuberculosis," In R. Bloom (ed.), Tuberculosis: Pathogenesis, Protection, and Control, ASM Press, Washington, D.C., pp. 47–59.
Bloom et al., "Tuberculosis: Commentary on a Reemergent Killer," Science, 257:1055–1064 (1992).
Gedde–Dahl, "Tuberculosis Infection in the Light of Tuberculin Matriculation," Am. J. Hyg. 56:139–214 (1952).
Sudre et al., "Tuberculosis: A Global Overview of the Situation Today," Bull Who 70:149–159 (1992).
Wayne, "Dormancy of Mycobacterium tuberculosis and Latency of Disease," Eur. J. Clin. Microbiol. Infec. Dis., 13:908–914 (1994).
Khomenko, "L–Transfermation of the Mycobacerial Population In the Process of Treating Patients with Newly Detected Destructive Pulmonary Tuberculosis," Probl. Tuberk, 2:18–23 (1980).
Werner, "Filterable Forms of Mycobacterium tuberculosis," Am. Rev. Tuberc., 69:473–474 (1953).
Ausubel et al., Current Protocols in Molecular Biology (John Wiley & Sons, Inc.), pp. 1.8.4–1.8.8 (1994).
Sambrook et al., Molecular Cloning: A Laboratory Manual (Cold Spring Harbor Lab. Press, Plainview, NY), pp. 9.31–9.57 (1989).
Wayne, Am. Rev. Resp. Dis., 114:807–811.
Firestein et al., Anal. Biochem, 167:381–386 (1987).
Lonetto et al., J. Bacteriol., 174:3843–3849 (1992).
Gross et al., in Transcriptional Regulation, eds. McKnight et al. (Cold Spring Harbor Lab. Press, Plainview, NY), 1:129–176 (1992).
Predich et al., Mol. Microbiol., 15:355–366 (1995).
Kempsell et al., Gen Microbiol, 138:1717–1727 (1992).
Honore et al., Mol. Microbiol, 7:207–214 (1993).
Tanaka et al., Science, 242:1040–1042 (1988).
Potuckova et al., Mol. Microbiol, 17:37–48 (1995).
Gholamhoseinian et al., J. Bacteriol, 171:5747–5749 (1989).
Margolis et al., Science, 254:562–565 (1991).
Benson et al., J. Bacteriol., 175:2347–2356 (1993).
Moran, "Measuring Gene Expression in Bacillus", In Molecular Biological Methods for Bacillus, C.R. Harwood and Cutting (ed.) Wiley & Sons, Chichester, England, pp. 267–293 (1990).

Lonetto et al., PNAS, 91:7573–7577 (1994).
Haines et al., Biotechniques, 12:736–740 (1992).
Spiegelman et al., "Purification of RNA Polymerase from Phage SP82–Infected Bacillus Subtillis," J. Biol. Chem., 249:1476–1482 (1974).
Benson et al., PNAS, 90:2330–2334 (1993).
Schmidt et al., PNAS, 87:9221–9225 (1990).
Alper et al., Cell, 77:195–205 (1994).
Schuler et al., Proteins Struct. Funct. Genet., 9:180–190 (1991).
Stanford et al., Tubercle, 68:241–242 (1987).
Csillag et al., "The Mycococcus form of Mycobacteria," J. Gen. Microbiol, 34:341 (1964).
Khomenko, "The Variability of Mycobacterium tuberculosis in Patients with Cavitary Pulmonary Tuberculosis in the Course of Chemotherapy," Tubercle, 68:243–253 (1987).
Barksdale et al., "Spheroidal Bodies and Globi of Human Leprosy," Biochem. Biophys Res. Comm., 54:290 (1973).
Chatterjee A Non–Acid Fast Coccoid Precursor—Possible Cultivable Phase of Mycobacterium Leprae, Leprosy in India, 48:398 (1976).
Rook et al., "Autoimmunity or Slow Bacterial Infection?" Immunol. Today, 13:160–164 (1992).
Fidler et al., "Mycobacterium tuberculosis DNA in Tissue Affected by Sarcoidosis," BMJ 306:546–549 (1993).
Haldenwang, Microbiol. Rev., 59:1–30 (1995).
Dufour et al., Interactions Between a Bacillus subtillisAnti–$\sigma$ Factor (RsbW) and its Antagonists (RsbV), J. Bacteriol, 176:1813–1820 (1994).
Kalman et al., "Similar Organization of the SigB and spoIIA Operons Encoding Alternative Sigma Factors of Bacillus subtilis RNA Polymerase," J. Bacteriol., 172:5575–5585 (1990).
Min et al., "$\sigma^F$, The First Compartment–Specific Transcription Factor of Bacillus subtilis, is Regulated by an Anti–Sigma Factor Which is also a Protein Kinase," Cell, 74:735–742 (1993).
Stock et al., "Protein Phosphorylation and Regulation of Adaptive Responses in Bacteria," Microbiol. Rev., 53:450–490 (1989).
Boylan et al., "Transcription Factor $\sigma^B$, of Bacillus subtilis Control a Large Stationary–Phase Regulon," J. Bacteriol, 175:3957–3963 (1993).
Burgess et al., "Purification of RNA Polymerase Sigma Factor," Methods Enzymol, 21:500–506 (1971).
Kumar et al., "An Improved Method for the Purification of DNA Dependent RNA Polymerase from E. Coli," J. Biochem Biophys. Methods, 15:235–240 (1988).

Primary Examiner—George C. Elliott
Assistant Examiner—Terry A. McKelvey
Attorney, Agent, or Firm—Cushman Darby & Cushman IP Group of Pillsbury Madison & Sutro LLP

[57] ABSTRACT

Two genes, orfX and orfY, regulate sigF expression and sigF activity in M. tuberculosis. M. tuberculosis sigF, orfX, and orfY are used in screening methods for potential therapeutic agents which regulate the growth of M. tuberculosis.

```
TCCAGACCTTCCACGACGGT CGCCAGCCCGATGTAGCCGG CAGTGTCTTCGGCATCACGT TGACCGCCCGACGGGCGGCA
                                                                              80

TCCAGCAG GTG ACG GCG CGC GCT GCC GGC GGT TCT GCA TCG CGA GCT AAC GAA TAC GCC GAC GTT
         M   T   A   R   A   A   G   G   S   A   S   R   A   N   E   Y   A   D   V>
                                                                              145/19
                                                                              208/40

CCG GAG ATG TTT CGC GAG CTG GTT GGT TTG CCT GCC GGC TCA CCG GAA TTC CAG CGG CAC CGG
 P   E   M   F   R   E   L   V   G   L   P   A   G   S   P   E   F   Q   R   H   R>
                                                                              271/61

GAC AAG ATC GTT CAG CGG TGC TTG CCG CTG GCC GAT CAC ATC GCG CGG GTC AAC GCC GGT CGC
 D   K   I   V   Q   R   C   L   P   L   A   D   H   I   A   R   V   N   A   G   R>
                                                                              334/82

GGC GAA CCG CGT GAC GAC CGT GAC CTT ATT CAG CGC GCG CGG GTC GTC AAC GCC GCG GTT CGC
 G   E   P   R   D   D   R   D   L   I   Q   R   A   R   V   V   N   A   A   V   R>
                                                                              397/103

TTC GAC GTG AAG ACC GGG TCG GAC TTC GTC TCC GTT GCG CCT ACC ATC ATG GGC GAG GTC
 F   D   V   K   T   G   S   D   F   V   S   V   A   P   T   I   M   G   E   V>
                                                                              460/124

CGA CGA CAC TTC CGC GAC AAC AGC GAC GCC TGG TCG GTC CCC CGG CGT CTC AAG GAA CTG CAT
 R   R   H   F   R   D   N   S   D   A   W   S   V   P   R   R   L   K   E   L   H>
                                                                              523/145

CTG CGG CTA GGT ACC GCC ACC GCC GAT TTG TCG CAG CGG CTC GGG CGG CCG TCG GCA TCG
 L   R   L   G   T   A   T   A   D   L   S   Q   R   L   G   R   P   S   A   S>
```

FIG. 2B

```
GAG CTC GCC GCG GAG CTC GGG ATG GAC CGC GCT GAG GTT ATC GAA GGT TTG CTG GCG GGT AGT
 E   L   A   A   E   L   G   M   D   R   A   E   V   I   E   G   L   L   A   G   S >
                                                                              586/166
TCC TAC CAC ACC TTG ACC TCC ATC GAC AGC GGC GGT GGC CAG ATC GAC GAT GAC GCC CGC ACA
 S   Y   H   T   L   T   S   I   D   S   G   G   Q   I   D   D   D   A   R   T >
                                                                              649/187
GAC ACC CTG GGC GAC GTG GAT GCG GGT CTT GAC CAG ATC GAG AAT CGG GAG GTG CTT GCA ATC ACA
 D   T   L   G   D   V   D   A   G   L   D   Q   I   E   N   R   E   V   L   A   I   T >
                                                                              712/208
TTG CTC GAG GCG TTG CCC GAG CGG GAA CGA ACG GTC TTG GTG CTC AGG TTC TTC CGT CGT CCG
 L   L   E   A   L   P   E   R   E   R   T   V   L   V   L   R   F   F   R   R   P >
                                                                              775/229
ACC CAA ACG CAG ATC GCC GAG CGC GAG CGC GTC GGT ATC TCA CAG ATG CAC GTG TCG CTG ATG
 T   Q   T   Q   I   A   E   R   E   R   V   G   I   S   Q   M   H   V   S   L   M >
                         261                                                  838/250
AAG TCA TTG GCA CGG CTA CGG GAT CAG TTG GAG TAG CCGCCGGGCTTACTTGGATCTC
 K   S   L   A   R   L   R   D   Q   L   E   *
                                           896
```

FIG. 3

```
MTBSIGF   vtaraaggsasraneyadvpe---------------------MFREL            26
SCORPOF   mpastapqappappaqaqaqapaqaqeapapqrsrgadtraltqvLFGEL          50
BSUSIGF   mdvevkknGKNAQLKDHEVKELIKQSQ------------------              27
BSUSIGB   mtqp-----SKTTKLTKDEVDRLISDYQ------------------             23

MTBSIGF   VGLPAGSPEFQRHRDKIVQRCLPLADHIARRFEGRGEPRDDLIQVARVGL          76
SCORPOF   KGLAPGTPEHDRVRAALIEANLPLVRYAAARFRSRNEPMEDVVQVGTIGL         100
BSUSIGF   -----NG-DQqARDLLIEKNMRLVWSVVQRFLNRGYEPDDLFQIGCIGL           70
BSUSIGB   -----TKQDEQAQETLVRVYTNLVDMLAKKYSKGKSFHEDLRQVGMIGL           67

MTBSIGF   VNAAVRFDVKTGSDFVSFAVPTTMGEVRRHFRDNSWSVKVPRRLKELHLR         126
SCORPOF   INAIDRFDPERGVQFPTFAMPTVVGEIKRYFRDNVRTVHVPRRLHELWVQ         150
BSUSIGF   LKSVDKFDLTYDVRFSTYAVPMIIGEIQRFIRDDG-TVKVSRSLKELGNK         119
BSUSIGB   LGAIKRYDPVVGKSFEAFAIPTIIGEIKRFLRDKTWSVHVPRRIKELGPR         117

MTBSIGF   LGTATADLSQRLGRAPSASELAAELGMDRAEVIEGLLAGSSYHTLSIDSG         176
SCORPOF   VNSATEDLTAFGRSPTTAEIAERLRITEEEVLSCIEAGRSYHATSLEAA          200
BSUSIGF   IRRAKDELSKTLGRVPTVQELADHIEIEAEDVVLAQEAVRApssihetvy         169
BSUSIGB   IKMAVDQLTTETQRSPKVEELAEFLDVSEEEVLETMEMGKSYQALSVDHS         167

MTBSIGF   GGSDDDARAITDTLGDVDAGLD---QIENREVLRPLLEALPERERTVLVL         223
SCORPOF   QEGDG-LPGLLDRLGYEDP---ALDGVEHRDLVRHLLVQLPEREQRILLL         246
BSUSIGF   ---E-NDGDPITLLDQIADNSEekwf--DKIALKEAISDLEEREKLIVYL         213
BSUSIGB   IEADS-DGSTVTLDIVGSQEDGYERVNQQLMLQSVLHVLSDREKQIIDL          216

MTBSIGF   RFFDSMTQTQIAERVGISQMHVSRVLAKSLARLRDQle-------              261
SCORPOF   RYYSNLTQSQISAELGVSQMHVSRLLARSFQRLRSAnrida----              287
BSUSIGF   RYYKDQTQSEVAERLGISQVQVSRLEKKILKQIKVQmdhtdg---              255
BSUSIGB   TYIQNKSQKETGDILGISQMHVSRLQRKAVKKLREAliedpsmelm             262
```

REGULATION OF A SIGMA FACTOR FROM *MYCOBACTERIUM TUBERCULOSIS*

This invention was made using U.S. government grants from the National Institutes of Health AI36973 and AI07417. Therefore the U.S. government retains certain rights to the invention.

TECHNICAL FIELD OF THE INVENTION

The present invention is broadly directed to reagents and methods for developing novel therapeutics for treating active and latent *M tuberculosis*.

BACKGROUND OF THE INVENTION

Tuberculosis is the leading cause of death due to infection, causing an estimated 2.5 million deaths and 7.5 million cases per year worldwide (1). In the United States, rates of tuberculosis began to increase in 1985 after 40 years of steady decline. In addition, a number of American cities are reporting high rates of infection by multiply drug resistant tuberculosis. Such mycobacteria cause a high mortality rate because available antibiotics are ineffective (2).

About 90% of individuals who become infected with *M. tuberculosis* do not have immediate symptoms but develop a positive reaction to the tuberculin skin test and carry the bacteria in a dormant or latent state (3). Over a lifetime, these individuals have a 10% risk of developing reactivation tuberculosis in which, after years of quiescence, the tubercle bacilli resume growth and cause classic pulmonary tuberculosis as well as other forms of disease. One billion people, roughly one-third of the world's population, have latent tuberculosis (4). Individuals with latent tuberculosis currently require prolonged therapy because antimycobacterial drugs work poorly against dormant bacilli.

Little is known regarding the state of dormant tuberce bacilli within the human host (5). There is a controversial body of literature describing filterable forms, granular bacillary bodies, and L-forms associated with tuberse bacilli (6, 7). These forms were reported as early as 1907 when Hans Much described granular non-acid-fast bacilli in tuberculous abscesses (31). The granules, which came to be known as Much's granules, were filterable, failed to grow in culture, and failed to produce typical tuberculosis when inoculated into animals. However, if tissue from the first animal was inoculated into a second, classic tuberculosis ensued. Similar observations have been reported over the decades for both tuberculosis (32, 33) and leprosy (34, 35). Dormant or altered mycobacterial forms have also been proposed as etiologic agents for granulomatous diseases such as sarcoidosis and inflammatory bowel disease (36). There have been reports of PCR-amplifiable, mycobacterial DNA in the tissues of patients with these diseases (37). There is a need in the art for reagents and methods for identifying therapeutic agents to treat active and latent tuberculosis.

SUMMARY OF THE INVENTION

It is an object of the invention to provide a DNA segment encoding an *M. tuberculosis* protein involved in latency regulation.

It is another object of the invention to provide preparations of an isolated protein from *M. tuberculosis* which is involved in latency regulation.

It is still another object of the invention to provide a polypeptide which is the product of a genetic fusion of an *M. tuberculosis* gene involved in latency regulation.

It is still another object of the invention to provide a method for screening potential therapeutic agents for the ability to trigger or inhibit the growth arrest of *M. tuberculosis*.

It is another object of the invention to provide a reporter construct for screening potential therapeutic agents.

It is yet another object of the invention to provide a method for screening potential therapeutic agents for use in regulating the growth of *M. tuberculosis*.

It is still another object of the invention to provide a method of identifying compounds which regulate the binding of two *M. tuberculosis* proteins involved in latency.

These and other objects of the invention are provided by one or more of the embodiments described below. In one embodiment of the invention an isolated and purified subgenomic DNA segment encoding an *M. tuberculosis* orfX is provided.

In another embodiment of the invention a preparation of an isolated orfX from *M. tuberculosis* is provided.

In yet another embodiment of the invention a preparation is provided which consists of an orfX polypeptide from *M. tuberculosis*.

In another embodiment of the invention a preparation is provided which consists of a polypeptide consisting of at least four contiguous amino acids of the sequence shown in SEQ ID NO:3.

In still another embodiment of the invention a polypeptide is provided. The polypeptide is the product of a genetic fusion of a first and second gene sequence, wherein the first sequence is all or a portion of an *M. tuberculosis* orfX gene and the second sequence encodes all or a portion of a second protein.

In still another embodiment of the invention an isolated and purified subgenomic DNA segment encoding an *M. tuberculosis* orfY is provided.

In another embodiment of the invention a preparation of an isolated orfY from *M. tuberculosis* is provided.

In yet another embodiment of the invention a preparation is provided which consists of an orfY polypeptide from *M. tuberculosis*.

In another embodiment of the invention a preparation is provided which consists of a polypeptide consisting of at least four contiguous amino acids of the sequence shown in SEQ ID NO:4.

In still another embodiment of the invention a polypeptide is provided. The polypeptide is the product of a genetic fusion of a first and second gene sequence, wherein the first sequence is all or a portion of a *M. tuberculosis* orfY gene and the second sequence encodes all or a portion of a second protein.

In yet another embodiment of the invention a reporter construct is provided. which comprises a sigF transcription regulatory region covalently linked in a cis configuration 5' of a gene encoding an assayable product, wherein transcription of the gene is regulated by the sigF transcription regulatory region.

In another embodiment of the invention a method is provided for screening potential therapeutic agents for the ability to trigger the growth arrest of *M. tuberculosis* by activating the expression of sigF, or to reactivate latent *M. tuberculosis* by inhibiting the expression of sigF. The method comprises the steps of: incubating a potential therapeutic agent with a cell which contains a sigF reporter construct, said reporter construct comprising a sigF transcription regulatory region covalently linked in a cis configuration to a downstream gene encoding an assayable product; and measuring the production of the assayable product, a potential therapeutic agent which increases the production by the cell of the assayable product being an agent which will trigger the growth arrest of *M. tuberculosis* by activating the expression of sigF, and a potential therapeutic agent which decreases the production by the cell of the assayable product being an agent which will reactivate *M. tuberculosis* by inhibiting the expression of sigF.

In still another embodiment of the invention a method is provided for screening potential therapeutic agents for use in modulating the growth of *M. tuberculosis* by regulating the activity of *M. tuberculosis* sigF. The method comprises the steps of: measuring in vitro transcription from the transcription construct incubated with *M. tuberculosis* sigF in the presence and absence of a test compound, the transcription construct comprising a gene coding sequence and a promoter which is responsive to *M. tuberculosis* sigF, the promoter being upstream from and adjacent to the gene, the in vitro transcription being effected in the presence and absence of a test substance; determining whether transcription of the gene is altered by the presence of said test substance, a test substance which alters the transcription of the gene being a candidate for use in regulating the growth of *M. tuberculosis*.

In yet another embodiment of the invention a method of identifying compounds which regulate the binding of *M. tuberculosis* sigF protein to orfX protein is provided. The method comprises the steps of: incubating *M. tuberculosis* sigF protein immobilized on a solid support with a test compound and *M. tuberculosis* orfX; determining the amount of the *M. tuberculosis* orfX protein which is bound to the *M. tuberculosis* sigF protein, a desirable test compound being one which increases or decreases binding of the *M. tuberculosis* orfX protein to *M. tuberculosis* sigF protein. The method may also comprise the steps of: incubating *M. tuberculosis* orfX protein immobilized on a solid support with a test compound and *M. tuberculosis* sigF protein; determining the amount of the *M. tuberculosis* sigF protein which is bound to the *M. tuberculosis* orfX protein, a desirable test compound being one which increases or decreases binding of the M. tuberculosis sigF protein to *M. tuberculosis* orfX protein.

These and other embodiment of the invention provide the art with reagents and methods for identifying therapeutic agents to treat active and latent tuberculosis.

BRIEF DESCRIPTION OF THE DRAWINGS

FIG. 1A shows the restriction map and open reading frame analysis of the *M. tuberculosis* sigF gene cluster. The relative positions of restriction sites, the sigF open-reading frame, and the positions of promoter consensus sites for *Streptomyces coelicolor* WhiG (SCOwhiG) and *Bacillus subtilis* SigF (BSUsigF) are shown. Numbers along the bottom line are in bp.

FIG. 1B shows the genetic organization of the *B. subtilis* sigF and *B. subtilis* sigB gene clusters for comparison. Diagram shows that the arrangement anti-anti-sigma→anti-sigma→sigma is conserved since spoIIAA and rsbV encode anti-anti-sigma, and spoIIAB and rsbW encode anti-sigmas.

FIGS. 2A–2B DNA and deduced protein sequence of the *M. tuberculosis* sigF region The 896 bp of *M. tuberculosis* DNA sequenced (nucleotides 1094 to 1989 in SEQ ID NO:1) is shown in FIGS. 2A and 2B along with the deduced protein sequence of sigF (SEQ ID NO:2). Numbers at right correspond to nucleotide/amino acid positions.

FIG. 3. Alignment of *M. tuberculosis* sigF with related sigma factors

The deduced amino acid sequences of *M. tuberculosis* sigF (SEQ ID NO:2) aligned with homologues using the MACAW algorithm (30). Capitalized blocks of amino acids represent segments with statistically significant homology scores. Black and gray shading indicates amino acid similarity (black being the highest). The length of each polypeptide is shown by the numbers on the right. BSUsigF =*Bacillus subtilis* sigF (Acc. No. M15744, SEQ ID NO:10), BSUSIGB =*Bacillus subtilis* SigB (Acc. No. M13927, SEQ ID NO:11), and SCOsigF=*Streptomyces coelicolor* sigF (Acc. No. L11648, SEQ ID NO:9).

Figure 4:
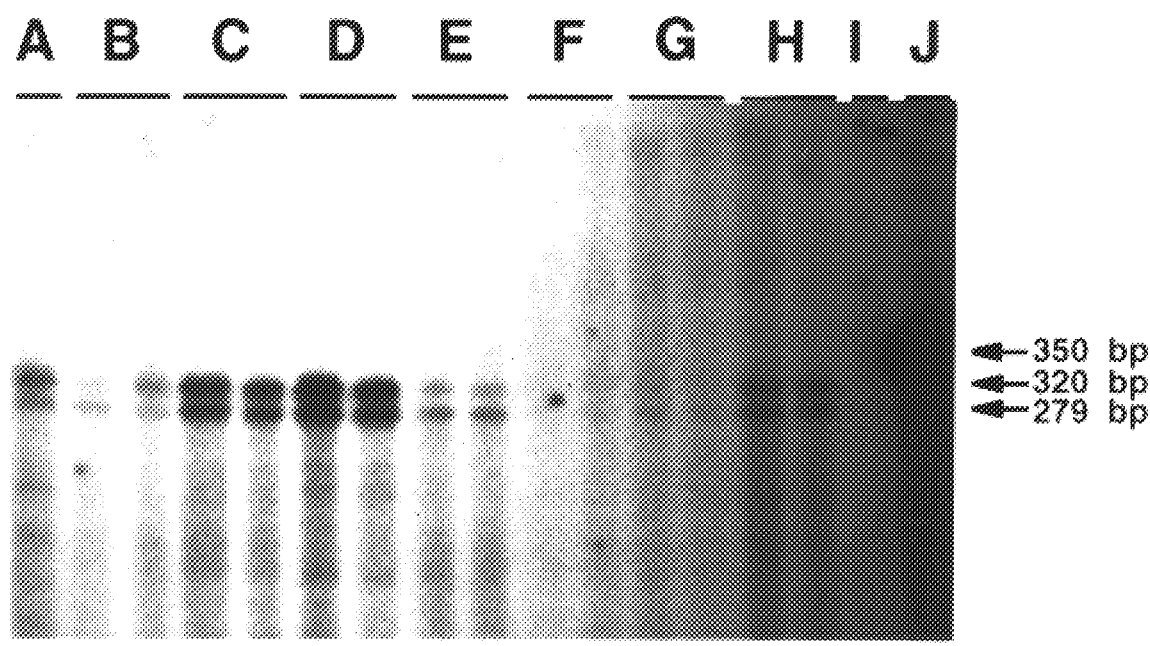

FIG. 4. RNase protection assay (RPA) with RNA extracts from *M. bovis* BCG exposed to different conditions.

Autoradiogram of RPA reaction products following liquid hybridization between total BCG RNA the pCK1845-derived sigF-specific antisense RNA probe separated on a 5% denaturing polyacrylamide gel and exposed to X-ray film for 24 hr. Samples B-H were assayed in duplicate. RPA was performed upon equivalent amounts of total RNA from *M. bovis* BCG cultures subjected to the following conditions: A, 10 mM $H_2O_2$; B, 5% EtOH; C, nitrogen depletion; D, cold shock; E, microaerophilic stress; F, early exponential growth ($A_{600}$=0.67); G, late exponential growth ($A_{600}$=1.5); H, stationary phase ($A_{600}$=2.7). Control samples were: I, an in vitro transcribed non-complementary probe (negative control); J, in vitro transcribed sense-strand sigF probe containing 350 complementary bases (positive control).

DETAILED DESCRIPTION OF THE INVENTION

It is a discovery of the present invention that *M. tuberculosis* sigF is regulated by *M. tuberculosis* orfX and orfY proteins. The *M. tuberculosis* sigF protein by itself or in combination with *M. tuberculosis* orfX and orfY can be used to screen for dormancy inducers which function as bacteriostatic antibiotics by triggering growth cessation during active tuberculosis infection. They can also be used to screen for antagonists useful as reactivation inducers to stimulate controlled reactivation in patients with latent tuberculosis. Reactivation will render antimycobacterial drugs more effective, because the drugs are typically more potent toward actively growing bacilli.

An *M. tuberculosis* sigF DNA segment can be isolated by amplifying sigma-like gene fragments from *M. tuberculosis* genomic DNA using polymerase chain reaction (PCR) with degenerate primers. Primers are designed to anneal to conserved regions of bacterial sigma factors. PCR fragments which are generated are subsequently used to screen an *M. tuberculosis* genomic library. The clones which hybridize to the PCR fragments are analyzed by restriction enzyme digestion and compared to the sigma factors from other species, i.e., *M. smegmatis*. The clones which show strong homology to the sigma factors previously described from other mycobacteria are further analyzed by standard DNA sequencing methods. The sequence of one such genomic clone is 2.8 kb. As shown in SEQ ID NO:1 the clone contains the *M. tuberculosis* sigma factor sigF gene, *M. tuberculosis* orfX gene, and *M. tuberculosis* orfY gene. The sequence reveals a 261 codon open-reading frame (nucleotides 1182–1964 in SEQ ID NO:1) encoding *M. tuberculosis* sigF protein as shown in SEQ ID NO:2. The sequence also reveals an open-reading frame encoding *M. tuberculosis* orfX protein. The open-reading frame is 242 codons (nucleotides 457–1182 in SEQ ID NO:1, amino acids 1 to 242 in SEQ ID NO:3), 208 codons (nucleotides 559–1182 in SEQ ID NO:1, amino acids 35 to 242 in SEQ ID NO:3), 168 codons (nucleotides 679–1182 in SEQ ID NO:1, amino acids 75 to 242 in SEQ ID NO:3), or 145 codon (nucleotides 748–1182 in SEQ ID NO:1, amino acids 98 to 2422 in SEQ ID NO:3) depending on which start codon is used. Similarly, the sequence reveals an open-reading frame encoding *M. tuberculosis* orfY protein. The open-reading frame is 137 codon (nucleotides 137–547 in SEQ ID NO:1, amino acids 1 to 137 in SEQ ID NO:4), 122 codon (nucleotides 182–547 in SEQ ID NO:1, amino acids 16 to 137 in SEQ ID NO:4), 120 codons (nucleotides 188–547 in SEQ ID NO:1, amino acids 18 to 137 in SEQ ID NO:4), or 103 codons (nucleotides 239–547 in SEQ ID NO:1, amino acids 35 to 137 in SEQ ID NO:4) depending on which start codon is used. Either one or more start codons may be used physiologically, for both orfX and orfY. It is well within the ability of a person skilled in the art to determine which start codon is used physiologically. For example, constructs employing different start codons can be expressed to produce polypeptides which can be tested for their ability to interact with sigF. The *M. tuberculosis* sigF gene and sigF protein are discussed in co-pending application (Bishal et al., DNA Encoding Stationary Phase, Stress response Sigma Factor from *Mycobacterium tuberculosis* Ser. No. 08/622,353, now U.S. Pat. No. 5,700,925, filed concurrently herewith.

A subgenomic DNA segment consisting of the nucleotide sequence shown in SEQ ID NO:1 or encoding a *M. tuberculosis* sigF protein, orfX protein, and orfY protein as shown in SEQ ID NOS: 2, 3, and 4 can be readily isolated and purified from a genomic clone or isolated directly from *M. tuberculosis* genomic DNA. Any known methods for subgenomic DNA segment isolation, e.g., PCR, or restriction enzyme digestion, can be used employing the sequence information disclosed in SEQ ID NO:1.

The DNA sequence provided herein can be used to form vectors which will replicate the sigF gene, orfX gene, or orfY gene in a host cell. DNA sequences which encode the same amino acid sequence as shown in SEQ ID NOS: 2, 3, or 4 can also be used, without departing from the contemplated invention. Variations from the sequence shown in SEQ ID NO:1 can be made, as is known in the art, employing alternate codon for the same amino acids, or employing alternate sequences in the non-coding region. A portion or all of the *M. tuberculosis* sigF gene, orfX gene, or orfY gene may also be cloned in-frame with a second protein-coding sequence to make a fusion protein. A portion of the desired gene may encode at least 4, 6, or 8 contiguous amino acids of the desired protein, and preferably the portion forms an immunogen or an epitope. The second protein-coding sequence may be all or a portion of a protein, which preferably is immunogenic and enhances the immune response to the desired protein, e.g., glutathione-S-transferase (GST) or hemagglutinin (HA). The second protein-coding sequence may encode at least 4, 6, or 8 contiguous amino acids of the protein. The products of the genetic fusion of the *M. tuberculosis* sigF gene, orfX gene, or orfY gene and the second protein are useful in generating antibodies specifically immunoreactive to *M. tuberculosis* sigF protein, orfX protein, or orfY protein.

Vectors typically contain an expression control sequence and preferably express all or a part, of the *M. tuberculosis* sigF protein, orfX protein or orfY protein. Suitable vectors, for expression of proteins in both prokaryotic and eukaryotic cells, are known in the art. Some vectors are specifically designed to effect expression of inserted DNA segments downstream from a transcriptional and translational control site. Selection of a vector for a particular purpose may be made using knowledge of the properties and features of the vectors, such as useful expression control sequences. Vectors may be used to transform host cells. Methods of transformation are known in the art, and may be used according to suitability for a particular host cell. Host cells may be selected according to their known characteristics. Non-mycobacterial cells are particularly desirable.

*M. tuberculosis* sigF protein, orfX protein, or orfY protein can be isolated from *M. tuberculosis* by any means known in the art. A part of the desired protein may be at least 4, 6, or 8 contiguous amino acids, which preferably forms an epitope. The proteins or the polypeptides can be prepared and isolated substantially free of other mycobacterial proteins from transformed non-mycobacterial host cells expressing the protein or the polypeptide. For example, antibodies which specifically bind to sigF protein, orfX protein, or orfY protein (see discussion below) can be employed for affinity purification. The procedures for protein purification are well known and routinely practiced in the art.

An antibody preparation which is specifically immunoreactive with *M. tuberculosis* sigF protein, orfX protein, or orfY protein may be obtained by standard techniques known in the art. Briefly, animals can be immunized with peptides along with adjuvants to generate polyclonal antibodies or hybridomas can be generated to obtain monoclonal antibodies. Antibodies may be polyclonal or monoclonal and may be raised using any protein containing *M. tuberculosis* sigF epitopes, orfX epitopes, or orfY epitopes as immunogens, including native *M. tuberculosis* sigF, orfX, or orfY protein, *M. tuberculosis* sigF fusion proteins, orfX fusion proteins, or orfY fusion proteins, or *M. tuberculosis* sigF peptides, orfX peptides, or orfY peptides. The antibodies are immunoreactive with sigF epitopes, orfX epitopes or orfY epitopes. Preferably the epitopes are present on other mycobacterial proteins.

Figure 1A:
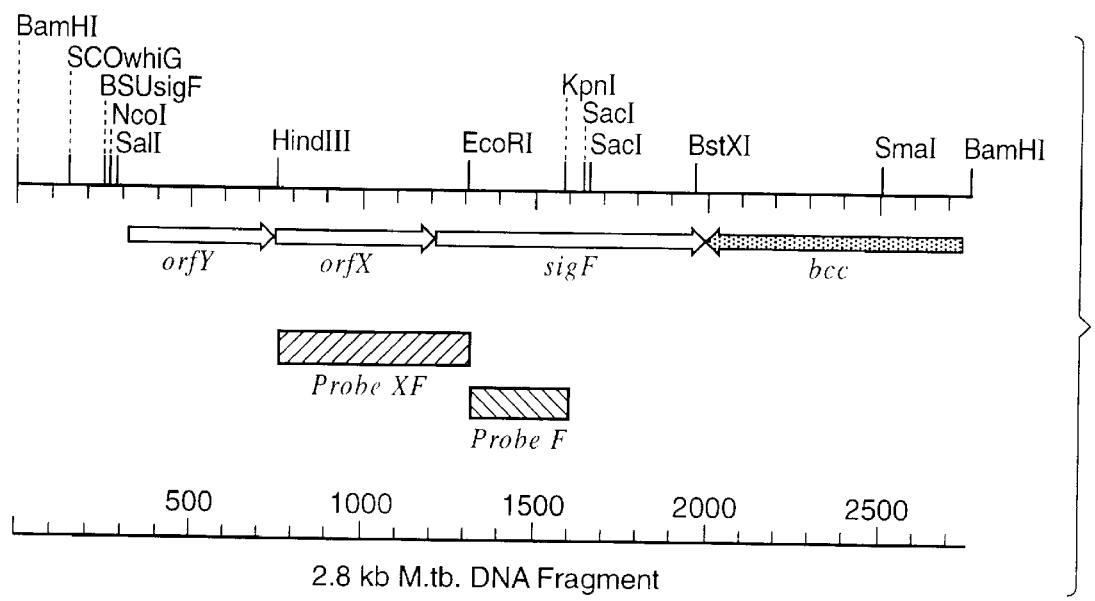
FIGS. 1A–1B. Map of 2.8 kb *M. tuberculosis* DNA fragment containing sigF
Figure 1B:
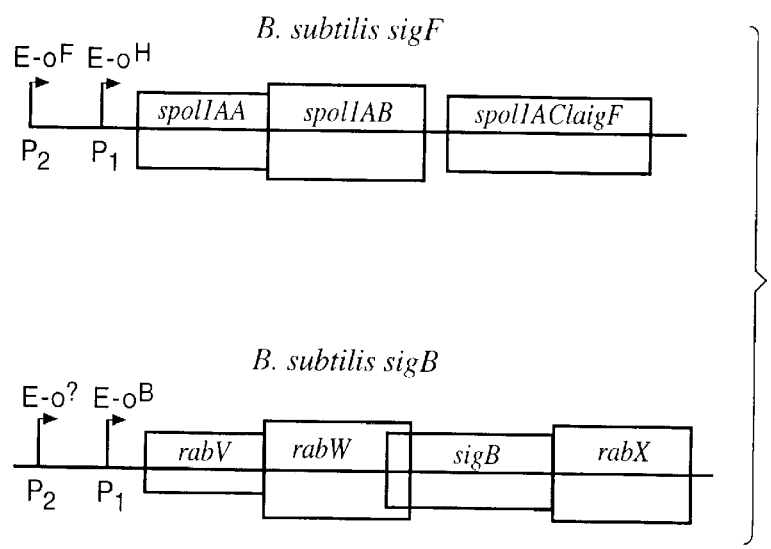

Though not wishing to be limited to any particular mechanism of action, it is postulated that *M. tuberculosis* orfX and orfY protein regulate sigF through the same mechanism employed by the SigF and SigB families in *B. subtilis*. The mechanism used in *B. subtilis* is a "partner-switching" mechanism between sigma factor, anti-sigma factor, and anti-anti-sigma factor. *B. subtilis* SigF is regulated by anti-sigma factor SpoIIAB and anti-anti-sigma factor SpoIIAA, the genes for both of which are co-transcribed with the SigF gene. *B. subtilis* SigB is activated by stress and starvation and controls a large regulon of stress response genes (43, 22). Similarly, SigB is controlled by anti-sigma factor RsbW (26) and an anti-anti-sigma factor RsbV (39), the genes for both of which are also co-transcribed with the SigB gene. Importantly, the arrangement of genes in the polycistronic messages for *B. subtilis* SigF family and SigB family is the same: anti-anti-sigma factor, anti-sigma factor, sigma factor as illustrated in FIG. 1B (40).

*M. tuberculosis* sigF, *B. subtilis* SigF and SigB protein have strong similarities to each other based on the database searches for protein homologues. An alignment of *M. tuberculosis* sigF, *B. subtilis* SigF and SigB proteins is shown in FIG. 3. Even though anti-sigma factors are a divergent family of protein kinases, RsbW shares 16% amino acid identity with orfX and SpoIIAB shares 13% identity with orfX. An alignment of these proteins reveals two blocks of homology which are common to a larger family of bacterial protein kinases (41, 42). Therefore in the *M. tuberculosis* sigF family, it is believed that orfX is an anti-sigma factor, and orfY is an anti-anti-sigma factor. Anti-sigma factors sequester sigma factors to negatively regulate the function of the sigma factors. The anti-sigma factor may switch to bind the anti-anti-sigma factor thereby releasing the inhibition.

Based on the present discoveries, screening methods have been devised to identify chemical agents which have use in therapy for treating active and latent tuberculosis. Potential therapeutic agents can be screened for the ability to activate or inhibit the expression of *M. tuberculosis* sigF gene. According to one method, the ability of a test substance or a potential therapeutic agent to activate or inhibit the expression of *M. tuberculosis* sigF gene is assessed by measuring the activity of a reporter construct in a cell. A reporter construct comprises a reporter gene, i.e. a gene encoding a conveniently assayable enzyme activity, such as chloramphenicol acetyltransferase or β-galactosidase, and a transcriptional regulatory region of *M. tuberculosis* sigF as shown in SEQ ID NO:1. The transcriptional regulatory region of *M. tuberculosis* sigF gene may comprise the sequence of nucleotides 1 to 1245 in SEQ ID NO:1. It may contain at least the sequence of nucleotides 1045 to 1245, 845 to 1245, 645 to 1245, 445 to 1245, or 245 to 1245 in SEQ ID NO:1. It may alternatively or additionally contain at least the sequence of nucleotides 1 to 245, 1 to 445, 1 to 645, 1 to 845, or 1 to 1045 in SEQ ID NO:1. It may alternatively or additionally also contain the sequence of nucleotides 1 to 200, 200 to 400, 400 to 600, 600 to 800, 800 to 1000, and 1000 to 1245. The reporter genes are covalently linked in a cis configuration with the regulatory region 5' of the reporter gene. Alternatively, the transcriptional region of *M. tuberculosis* sigF gene may contain part of the coding region of the sigF gene e.g. nucleotides 1 to 1280 in SEQ ID NO:1 and may be fused in-frame with the reporter gene.

Methods for measuring transcriptional or translational activity in vivo can be any which are known in the art. For example, a nuclear run on assay may be employed to measure the transcription of the reporter gene. The translation of the reporter gene may be measured by determining the activity of the translation product of the reporter gene. Methods for measuring the activity of an assayable product of certain reporter genes are well known in the art. In a preferred embodiment, the assayable product is measured in mycobacteria growing in rich medium when sigF activity is expected to be low. In another preferred embodiment, the assayable product is measured in mycobacteria in a stressed condition, e.g., nitrogen starvation, when sigF activity is expected to be high.

Potential therapeutic agents can also be screened for use in regulating the growth of *M. tuberculosis* by their ability to regulate the activity of *M. tuberculosis* sigF protein. The ability of a test compound or a potential therapeutic agent to regulate the activity of *M. tuberculosis* sigF protein is assessed by measuring the transcription of a gene in a transcription construct in vitro. A transcription construct comprises a promoter responsive to *M. tuberculosis* sigF protein and a gene. The gene in the transcription construct could be any gene known in the art. In a preferred embodiment, the length of the transcript of the gene is less than 200 bp and no more than 600 bp. The promoter in the transcription construct can be any to which *M. tuberculosis* sigF protein binds and which it activates. The promoter is responsive to *M. tuberculosis* sigF protein which induces the transcription of the gene downstream from and adjacent to the promoter. One such promoter comprises the sequence of nucleotides 1 to 350 in SEQ ID NO:1. Suitable methods for measuring in vitro transcription are any known in the art. In vitro transcription may be carried out by incubating a transcription construct with *M. tuberculosis* sigF protein, labeled nucleotides, e.g., $^{32}$P-ATP, core RNA polymerase, nucleotides, and buffer reagents in the presence and absence of a test compound. The procedures for purifying core RNA polymerase from mycobacteria are well described in the art (44, 45, 46, 47). The conditions for in vitro transcription are well known in the art. The labeled transcript can be detected by gel electrophoresis and measured by any technique known in the art. Optionally, in vitro transcription can be carried out in the presence of *M. tuberculosis* orfX protein or both *M. tuberculosis* orfX and orfY protein.

A potential therapeutic agent which increases the production of the assayable product in the cell indicates its ability to increase the expression of *M. tuberculosis* sigF. A potential therapeutic agent which increases the level of in vitro transcription indicates its ability to enhance the activity of the transcriptional activating *M. tuberculosis* sigF protein. Test compounds which increase the expression of *M. tuberculosis* sigF gene or the activity of the sigF protein can trigger the growth arrest of *M. tuberculosis*. These compounds can be administered to a human with active tuberculosis, especially those who respond poorly to conventional antibiotic treatments. These compounds can induce growth arrest of *M. tuberculosis*, and initiate dormancy during severely advanced progressive tuberculosis or multi-drug resistant tuberculosis.

A test substance which decreases the production of the assayable product in the cell indicates its ability to decrease the expression of *M. tuberculosis* sigF. A test substance which decreases the level of in vitro transcription indicates its ability to inhibit the activity of the *M. tuberculosis* sigF protein. Test compounds which decrease the expression of *M. tuberculosis* sigF or the activity of the sigF protein can reactivate latent *M. tuberculosis*. These compounds can be used in the treatment of active tuberculosis to neutralize the sigF protein and prevent mycobacterial adaptation so that mycobacteria can not make the changes necessary to evade the host immune system and enter an antibiotic-insensitive latent state. These compounds can also be used in the treatment of latent tuberculosis to neutralize the sigF protein and force the mycobacteria to reactivate in a controlled fashion so that they may be inhibited and/or killed quickly and efficiently using antibiotics. The compound and the antibiotic can be administered either (a) simultaneously (optionally by formulating the two together in a common carrier), or (b) at different times during the course of a common treatment schedule. In the latter case, the two compounds are administered at times sufficiently close for the antibiotic to efficiently kill or inhibit the growth of the reactivated *M. tuberculosis*. This may be within one month, one week, one day or one hour According to another embodiment of the invention, compounds regulating the binding between *M. tuberculosis* sigF protein and orfX protein may be identified. *M. tuberculosis* sigF protein can be attached to an insoluble polymeric support such as agarose, cellulose, or the like. A test compound is incubated with the immobilized sigF protein in the presence of *M. tuberculosis* orfX protein or both orfY and orfX protein. Alternatively, orfX protein can be immobilized on a solid support and a test compound can be incubated with the immobilized orfX protein in the presence of *M. tuberculosis* sigF protein or both sigF and orfY protein. The conditions for binding among anti-sigma factor, sigma factor, and anti-anti-sigma factor are well characterized and known in the art. Particularly, Alper et al., *Cell* vol 77, 195–206 (1994) describes the binding conditions for SpoIIAA, SpoIIAB, and sigma factor. After incubation, all non-binding components can be washed away, leaving orfX protein bound to the sigF protein/solid support or sigF protein bound to the orfX protein/solid support. The amount of orfX or sigF can be quantified by any means known in the art. For example, it can be determined using an immunological assay, such as ELISA, RIA, or Western blotting. The amount of bound orfX or sigF is determined with and without the test compound. A desirable compound is one which increases or decreases the binding of orfX protein to *M. tuberculosis* sigF protein in the presence or absence of orfY protein.

The following examples are provided for exemplification purposes only and are not intended to limit the scope of the invention.

EXAMPLE 1
PCR with degenerate sigma-70 consensus primers successfully identifies an *M. tuberculosis* sigma factor gene, sigF Degenerate primers Y207 (5'-AACCTGCGHCTSGTSGTC-3' SEQ ID NO:5, a forward primer for the hexapeptide, NLRLVV SEQ ID NO:6) and Y208 (5'-CTGNCGKATCCACCASGTSGCRTA-3' SEQ ID NO:7, a reverse primer for the octapeptide, YATWWIRQ SEQ ID NO:8) were used to amplify sigma factor gene fragments from *M. tuberculosis* genomic DNA in standard PCR reactions with Taq polymerase (Gibco-BRL, Gaithersburg, MD): 30 cycles, 94° C. for 60 sec, 54° C. for 90 sec, and 72° C. for 120 sec. PCR products were cloned and used as probes to select genomic clones from an *M. tuberculosis* H37Rv cosmid library (kindly provided by K. de Smet). Analysis of bacterial sigma factors reveals considerable conservation in regions 2.1–2.4 and 4.1–4.2 (12). Region 2.1 is implicated in core polymerase-binding while the 2.3/2.4 and 4.2 regions are believed to contact the −10 and −35 regions, respectively, of the promoter DNA consensus sequence (13). We designed degenerate primers Y207 and Y208 directed towards conserved regions 2.1 and 2.3, respectively, and used them to amplify sigma-like gene fragments from *M. tuberculosis* genomic DNA. These primers amplified several distinct products including the anticipated 165 bp fragment. This 165 fragment was likely to consist of a mixture of sequences since it hybridized strongly to two separate *M. tuberculosis* BamHI fragments (4.8 kb and 2.8 kb) by Southern analysis. *E. coli* cosmid clones which hybridized with the 165 bp PCR product were selected by screening an *M. tuberculosis* H37Rv library, and the 2.8 kb BamHI fragment was subcloned as pYZ99 from one of these cosmids. A restriction map of the 2.8 kb BamHI fragment is shown in FIG. 1. The 4.8 kb BamHI fragment was identical to a 7 kb fragment from *M. tuberculosis* which had already been sequenced (S. Cole and I. Smith, personal communication). This fragment also showed strong homology to one of the sigma factors previously described from *M. smegmatis* (14).

Sigma factors are subunits of bacterial RNA polymerase and confer promoter specificity to the holoenzyme complex. The unique affinity of each sigma factor for its promoter consensus sequence is an essential component in many gene regulation systems. For example, in *Bacillus subtilis*, sporulation is regulated by a carefully-coordinated cascade of alternate sigma factors and the genes which they control (38).

The structure and function of sigma factors are conserved across species, and these regions of conservation may be exploited to identify new sigma factors (17). We successfully employed PCR using degenerate primers based on conserved regions 2.1 and 2.3 to identify a new *M. tuberculosis* sigma factor gene, sigF.

EXAMPLE 2
The sequence of the *M. tuberculosis* sigma factor gene, sigF

DNA sequencing was performed with an Applied Biosystems 373 automated DNA sequencer (Foster City, Calif.) using dye terminator chemistry at the Biopolymer lab of the Howard Hughes Medical Institute at The Johns Hopkins University School of Medicine.

A combination of primer walking and subcloning of restriction fragments was used to determine the DNA sequence of 896 bp of pYZ99 which contains the sigma factor gene, sigF as shown in FIGS. 2A and 2B. Each base was sequenced an average of 5 times (minimum 3, maximum 8). The sequence reveals a 261 amino acid open-reading frame. The 88 bp of upstream sequence does not contain significant homology to *E. coli* sigma-70 promoter consensus sequences, nor does it have a clear-cut Shine-Dalgarno ribosome binding site with complementarity to the 3' end of the *M. tuberculosis* 16SrRNA sequence (15). Nevertheless, the sigF gene is clearly transcribed in slow-growing mycobacteria (see below). Our assignment of the initiation codon is based on alignments with other known sigF-like proteins (see below) and the observation that GTG is commonly used as an initiation codon in mycobacteria (16).

EXAMPLE 3
Homologues of SigF

The 261 aa deduced protein encoded by *M. tuberculosis* sigF has significant homology to the known stress and sporulation-specific sigma factors from Bacillus spp. and Streptomyces spp. The closest similarities are to *S. coelicolor* SigF (41% identity and 62% similarity), *B. subtilis* SigB (30% identity and 50% similarity) and *B. subtilis* SigF (26% identity and 44% similarity). An alignment of the deduced *M. tuberculosis* SigF protein sequence with these three other sigma factors is shown in FIG. 3. In addition, a partial SigF homologue is present in *M. leprae* (Acc. No. U00012); frameshift sequencing errors in the *M. leprae* sigF sequence may explain the incompleteness of this open-reading frame.

*M. tuberculosis* SigF has closest homology to *S. coelicolor* SigF, *B. subtilis* SigF, and *B. subtilis* SigB. The *S. coelicolor* SigF gene encodes a late-stage, sporulation-specific sigma factor. *S. coelicolor* SigF knockout mutants are unable to sporulate effectively producing deformed, thin-walled spores (18). *B. subtilis* SigF is essential for early spore gene expression. It is not transcribed until shortly after the start of sporulation (19), and its protein product is specifically activated within the developing forespore following septation (20). The *B. subtilis* SigB gene encodes a stress response sigma factor. While not an essential gene for growth or sporulation, SigB transcription is activated during stationary phase or under environmental stress, such as heat or alcohol shock (21, 22).

Lonetto et al. (12, 23) have divided the known sigma factors into a number of families based upon their primary structure homology patterns. The families include: primary sigma factors, a sporulation-specific group, a heat shock-related group, a flagellar-related group and the newly recognized extracytoplasmic family. An important implication of these sequence homology clusters is that correlations between the primary structure and general function of bacterial sigma factors is preserved even across species barriers.

The homology profile of *M. tuberculosis* SigF places it in the sporulation-specific family of such sigma factor classifications. This observation suggests that *M. tuberculosis* sigF has a functional role akin to those of the *S. coelicolor* and *B. subtilis* sigma factors to which it is similar.

EXAMPLE 4
Other mycobacteria which contain sigF-like genes

Southern blots were made from PvuII digested, mycobacterial genomic DNA obtained from clinical isolates kindly provided by J. Dick. The blots were probed with a 221 base pair, *M. tuberculosis* -specific probe (base pairs 438 to 659) according to a previously published protocol (9). Hybridizations were performed overnight at 55° C. and were followed by five washes in 3×SSC at 45° C.

Southern blots of PvuII digested, mycobacterial, genomic DNA revealed sigF cross-hybridization in several slow-growing mycobacteria including *M. bovis* BCG (ATCC 35734) and clinical isolates of *M. avium, M. triviale,* and *M. gordonae*. The rapid growing species, *M. segmatis* and *M. abscessus*, showed not hybridization by Southern blot analysis at intermediate stringency.

*M. tuberculosis* sigF-like sequences were identified by Southern blot analysis in several slow growing mycobacterial species including *M. bovis* BCG and *M. avium*. *M. leprae* was known prior to this study to possess a sigF homologue on cosmid B1308 (Acc. No. U00012). Rapid growing species, such as *M. segmatis and M. abscessus*, showed no hybridization by Southern blot. It is intriguing to postulate that the mycobacterial sigF gene might be associated with a developmental response unique to slow-growers. Alternatively, the absence of a sigF cross-hybridization in the rapidly growing species may simply be a function of increased evolutionary distance and decreased base pair homology.

EXAMPLE 5
Stress and stationary phase induction of sieF MRNA

Strains and Plasmids pYZ99 is pUC18 containing a 2.8 kb BamHI fragment of *M. tuberculosis* genomic DNA. pCK1845 is pCRII (Invitrogen, San Diego, Calif.) containing a 279 bp EcoRI/KpnI subclone of the *M. tuberculosis* sigF gene with an SP6 promoter site and a BamHI site at the 5' end of the sigF gene fragment and a T7 promoter site and an EcoRV site at the 3' end. Recombinant plasmids were constructed and transformed into *E. coli* DH5_by electroporation using standard protocols (8), and they were isolated and purified using the Qiagen system (Qiagen, Inc., Chatsworth, Calif.).

Mycobacterial cultures

Early exponential, late-exponential, and stationary phase Bacille Calmette-Guerin (BCG, Pasteur strain, ATCC 35734) cultures were grown in standard Middlebrook 7H9 broth (Difco Laboratories, Detroit, Mich.) supplemented with ADC and Tween 80 (ADC-TW, ref. 11) at 37° C. with constant shaking. For cold shock, log phase cultures ($A_{600}$= 0.78) were placed at 4° C. for 24 hours prior to harvesting. To test other stress conditions, log-phase cultures were centrifuged and resuspended in a stress broth at 37° C. with shaking for 24 hours. Stress broths consisted of Middlebrook 7H9-ADC-TW plus 10 mM $H_2O_2$ (oxidative stress) or 5% ethanol (alcohol stress). Nitrogen depleted medium was Middlebrook 7H9 containing only 10% of the standard amounts of glutamine and $NH_4Cl$. Microaerophilic cultures were prepared according to the settling method described by Wayne (10) for 7 days.

RNA Extraction and Quantification

Mycobacterial pellets were resuspended in extraction buffer (0.2M Tris, 0.5M NaCl, 0.01M EDTA, 1% SDS) plus an equal volume of phenol:chloroform:isoamyl alcohol (25:24:1). A 0.4 g aliquot of 300 µm prewashed glass beads (Sigma Chemical Company, St Louis, Mo.) was added and the samples were vortexed for 2 minutes at high speed. After a brief centrifugation, the aqueous phase was removed, re-extracted with phenol:chloroform:isoamyl alcohol, and finally extracted with chloroform: isoamyl alcohol (24:1). The purified RNA was ethanol precipitated and quantified by $A_{260}$ measurement. Specific mRNA levels were determined by RNase protection assay (RPA, ref. 11) using a $^{32}P$-labeled, in vitro transcribed, sigF antisense RNA probe derived from BamHI-cut pCK1845 (Maxiscript system, Ambion, Austin, Tex.). Control, nonlabeled sigF sense RNA was produced using the same DNA template cut with EcoRV, transcribed in the opposite direction. For each assay equal quantities of total mycobacterial RNA were tested.

Transcription of sigF was detected and monitored under different growth conditions of BCG, a slow-growing attenuated *M. bovis* strain which is a member of the *M. tuberculosis* complex, using an RNase protection assay (RPA, see FIG. 4). Our ability to protect a $^{32}P$-labeled sigF antisense RNA probe using total RNA isolated from BCG using RPA analysis confirms that sigF is a transcribed gene in this close relative of *M. tuberculosis*. Replicate experiments showed that the RPA signal intensity results were reproducible to within 20% when performed with different batches of RNA on different days. The twin protected bands at 320 and 279 bases (FIG. 4) were observed consistently with the pCK1845-derived sigF antisense RNA probe. Secondary structure analysis of our probe reveals that about 40 bases of vector sequences at its 3' end are capable of forming a stem-loop which would protect a larger portion of the probe than the expected 279 bases. Both bands chase to 350 bases when a non-labeled, sense-strand RNA complementary over 350 bases is added. Hence we believe that both bands result from protection of the probe by sigF mRNA.

In BCG cultures, sigF transcription was most strongly induced during stationary phase ($A_{600}$=2.7), nitrogen depletion, and cold shock. A weak RPA signal was present during late-exponential phase ($A_{600}$=1.5), oxidative stress (10 mM $H_2O_2$), microaerophilic culture conditions, and alcohol shock (5% ethanol). No sigF mRNA was detected during early exponential phase growth ($A_{600}$=0.67). The relative intensities of the RPA signals during different growth conditions is summarized in Table 1.

TABLE 1 sigF RPA signal relative to baseline for BCG grown under different conditions

| Growth Condition | RPA Signal Intensity* (relative to baseline) |
|---|---|
| Early Exponential Phase ($A_{600}$ = 0.67) | 1.0 |
| Late Exponential Phase ($A_{600}$ = 1.5) | 3.6 |
| Stationary Phase ($A_{600}$ = 2.7) | 9.8 |
| Oxidative Stress (10 mM $H_2O_2$) | 4.8 |
| Alcohol Shock (5% ethanol) | 2.8 |
| Cold Shock (4° C.) | 17.6 |
| Nitrogen Depletion | 8.8 |
| Microaerophilic Stress | 3.2 |

*Equal amounts of total bacterial RNA (0.85 µg) were used in each assay. Duplicate or quadruplicate aliquots of each stress culture were processed independently and average values are shown above. Quantitation was performed by digitally photographing the autoradiogram on an Ambis camera and then analyzing the bands on the NIH Imager program. Baseline was defined as the signal intensity at 279–320 nt. of early exponential phase samples which was essentially the same as background.

RNase protection assays using an *M. tuberculosis* sigF-specific probe showed that the *M. tuberculosis* sigF open reading frame is a transcribed gene. Transcription was maximal during stationary phase, cold shock, and nitrogen depletion. Weaker RPA signals were present during other stress conditions, such as oxidative stress, alcohol shock, and microaerophilic stress. No evidence of transcription was seen during exponential-phase growth. RPA is highly sensitive and can detect MRNA at the femtogram level (24). These findings show that the *M. tuberculosis* sigF gene encodes a stationary phase/stress response sigma factor. This pattern of induction is similar to that of the *B. subtilis* sigB gene.

*M. tuberculosis* can survive for relatively long periods in expectorated sputum. Survival outside the human host requires adaptation to oxidative stress, low nutrient levels, and low temperature. The biochemical and genetic alterations permitting the organism to survive under these conditions are unknown. All of these conditions, in particular cold shock, induce *M. tuberculosis* sigF transcription. Thus it is likely that sigF is involved in survival outside of the host. Alternatively, *M. tuberculosis* sigF might be involved in the adaptation of the organism during latent infection. The observation that *M. tuberculosis* has a sigma factor closely related to sporulation sigmas from *S. coelicolor* and *B. subtilis* is intriguing since tubercle bacilli are classically described as non-sporulating bacilli. Both the *B. subtilis* sigB and sigF genes are transcribed as parts of polycistronic messages containing post-translational regulatory genes (25–39). The sigB operon encodes three other genes (rsbV, rsbW, and rsbX) which control SigB activation. The *B. subtilis* sigF operon encodes two other genes encoding an anti-sigma factor (SpoIIAB) and an anti-anti-sigma factor (SpoIIAA). The *S. coelicolor* sigF gene appears to be monocistronic (18). Molecular genetic studies using the *M. tuberculosis* sigF gene may help address the question of whether tubercle bacilli enter a spore-like state during persistent infection.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

References

1. Smith, P. G., and A. R. Moss. 1994. Epidemiology of tuberculosis.

In B. R. Bloom (ed.) Tuberculosis: Pathogenesis, Protection, and Control. ASM Press, Washington, D.C., pp.47–59.

2. Bloom, B. R. and C. J. L. Murray. 1992. Tuberculosis: commentary on a reemergent killer. Science 257:1055–1064.
3. Gedde-Dahl, T. 1952. Tuberculous infection in the light of tuberculin matriculation. Am. J. Hyg. 56:139–214.
4. Sudre, P., G. ten Dam, A. Kochi. 1992. Tuberculosis: a global overview of the situation today. Bull. WHO 70:149–159.
5. Wayne, L. G. 1994. Dormancy of *Mycobacterium tuberculosis* and latency of disease. Eur. J. Clin. Microbiol. Infect. Dis. 13:908–914.
6. Khomenko, A. G. 1980. L-transformation of the mycobacterial population in the process of treating patients with newly detected destructive pulmonary tuberculosis. Probl. Tuberk. 2:18–23.
7. Werner, G. H. 1954. Filterable forms of *Mycobacterium tuberculosis*. Am. Rev. Tuberc. 69:473–474.

8. Ausubel, F. M., Brent, R., Kingston, R. E., Moore, D. D., Seidman, J. G., Smith, J. A., Struhl, K. (1994) *Current Protocols in Molecular Biology* (John Wiley and Sons, Inc.), pp.1.8.4–1.8.8.
9. Sambrook, J., Fritsch, E. F., Maniatis, T. (1989) *Molecular Cloning: A Laboratory Manual* (Cold Spring Harbor Lab. Press, Plainview, N.Y.), pp. 9.31–9.57.
10. Wayne, L. G. (1976) *Am. Rev. Resp. Dis.* 114, 807–811.
11. Firestein, G. S., Gardner, S. M., Roeder, W. D. (1987) *Anal. Biochem.* 167, 381–386.
12. Lonetto, M., Gribskoy, M., Gross, C. A. (1992) *J. Bacteriol.* 1764, 3843–3849.
13. Gross, C. A., Lonetto, M., Losick, R. (1992) in *Transcriptional Regulation*, eds. McKnight, S. L. & Yamamoto K. R. (Cold Spring Harbor Lab. Press, Plainview, N.Y.), Vol. 1, pp.129–176.
14. Predich, M., Doukhan, L., Nair, G., Smith, J. (1995) *Mol. Microbiol.* 15, 355–366.
15. Kempsell, K. E., Ji, Y. E., Estrada, I. C., Colston, M. J., Cox, R. A. (1992) J. *Gen . Microbiol.* 138, 1717–1727.
16. Honore, N., Bergh, S., Chanteau, S., Doucet-Populaire, F., Eiglmeier, K., Garnier, T., Georges, G., Launois, P., Limpaiboon, T., Newton, S., Niang, K., del Portillo, P., Ramesh, G. R., Reddi, P., Ridel, P. R., Sittisombut, N. Wu-Hunter, S., Cole, S. T. (1993) *Mol. Microbiol.* 7, 207–214.
17. Tanaka, K., Shina, T., Takahashi, H. (1988) *Science* 242, 1040–1042.
18. Potuckova, L., Kelemen, G. H., Findlay, K. C., Lonetto, M. A., Buttner, M. J., Kormanec, J. (1995) *Mol. Microbiol.* 17, 37–48.
19. Gholamhoseinian, A., Piggot, P. J. (1989) *J. Bacteriol.* 171, 5747–5749.
20. Margolis, P., Driks, A., Losick, R. (1991) *Science* 254, 562–565.
21. Benson, A. K., Haldenwang, W. G. (1993) *J. Bacteriol.* 175, 2347–2356.
22. Boylan, S. A., Redfield, A. R. Brody, M. S., Price, C. W. (1993) *J. Bacteriol.* 175, 7931–7937.
23. Lonetto, M., Brown, K. L., Rudd, K., Buttner, M. J. (1994) *Proc. Natl. Acad. Sci.* USA 91, 7573–7577.
24. Haines, D. S., Gillespie, D. H. (1992) *Biotechniques* 12, 736–740.
25. Kalman S., Duncan, M., Thomas, S., Price, C. W. (1990) *J. Bacteriol.* 172, 5575–5585.
26. Benson, A. K., Haldenwang, W. G. (1993) *Proc. Natl. Acad. Sci. USA* 90, 2330–2334.
27. Schmidt, R., Margolis, P., Duncan, L., Coppolecchia, R., Moran C. P. Jr., Losick, R. (1990) *Proc. Natl. Acad. Sci. USA* 87, 9221–9225.
28. Min, K. T., Hilditch, C. M., Dieterch, B., Prrington, J., Yudkin, M. D. (1993) *Cell* 74, 735–742.
29. Alper, S., Duncan, L., Losick, R. (1994) *Cell* 77, 195–205.
30. Schuler, G. D., Altschul, S. F., and Lipman, D. J. (1991). *Proteins Struct. Funct. Genet.* 9, 180–190.
31. Stanford, J. L. 1987. Much's granules revisited. Tubercle 68:241–242.
32. Csillag, A. 1964. The *Mycococcus form of mycobacteria. J. Gen. Microbiol.* 34:341.

33. Khomenko, A. G. 1987. The variability of *Mycobacterium tuberculosis* in patients with cavitary pulmonary tuberculosis in the course of chemotherapy. Tubercle 68:243–253.
34. Barksdale, L., J. Convit, K.-S. Kim , M. E. de Pinardi. 1973. Spheroidal bodies and globi of human leprosy. Biochem. Biophys. Res. Comm. 54:290.
35. Chatterjee, B. R. 1976. A non-acid fast coccoid precursor—possible cultivable phase of *Mycobacterium leprae*. Leprosy in India 48:398.
36. Roek, G. A. W., and J. L. Stanford. 1992. Autoimmunity or slow bacterial infection? Immunol. Today 13:160–164.
37. Fidler, H. M., G. A. Rook, N. McI. Johnson, and J. McFadden. 1993. *Mycobacterium tuberculosis* DNA in tissue affected by sarcoidosis. BMJ 306:546–549.
38. Haldenwang, W. G. 199 5 *Microbiol. Rev.* 59, 1–30.
39. Dufour, et al. 1994. Interactions between a *Bacillus subtilis anti-σ*factor (RsbW) and its antagonist (RsbV). *J. Bacteriol.*, 176:1813–1820
40. Kalman, et al. 1990. Similar organization of the sigB and spoIIA operons encoding alternative sigma factors of *Bacillus subtilis* RNA polymerase. *J. Bacteriol.* 172:5575–5585.
41. Min et al. 1993. $\sigma^F$, the first compartment-specific transcription factor of *Bacillus subtilis*, is regulated by an anti-sigma factor which is also a protein kinase. *Cell.* 74:735–742.
42. Stock, et al. 1989. Protein phosphorylation and regulation of adaptive responses in bacteria. *Microbiol. Rev.* 53:450–490.
43. Boylan et al. 1993. Transcription factor $\sigma^B$ of *Bacillus subtilis* controls a large stationary-phase regulon. *J. Bacteriol* 175:3957–3963.
44. Burgess et al. 1971. Purification of RNA polymerase sigma factor. *Methods Enzymol.* 21:500–506.
45. Kumar et al. 1988. An improved method for the purification of DNA dependent RNA polymerase from *E. coli*. *J. Biochem Biophys. Methods* 15:235–240.
46. Moran et al. 1990. Measuring gene expression in Bacillus. In Molecular Biological Methods for Bacillus. C. R. Harwood and Cutting (ed.) Wiley & Sons, Chichester, England, pp. 267–293.
47. Spiegelman et al. 1974. Purification of RNA polymerase from phage SP82-infected *Bacillus subtilis*. *J. Biol. Chem.* 249:1476–1482.

---

We claim:

1. An isolated and purified subgenomic DNA segment encoding a *Mycobacterium tuberculosis* orfX, which orfX comprises amino acids 98 to 242 of the sequence set forth as SEQ ID NO:3.

2. A vector comprising the DNA segment of claim 1.

3. The vector of claim 2 further comprising expression control sequences.

4. A host cell transformed with the DNA segment of claim 1.

5. A host cell transformed with the vector of claim 2.

6. An isolated and purified subgenomic DNA. segment encoding a *Mycobacterium tuberculosis* orfY, which orfY comprises amino acids 35 to 137 of the sequence set forth as SEO ID NO:4.

7. A vector comprising the DNA segment of claim 6.

8. The vector of claim 7 further comprising expression control sequences.

9. A host cell transformed with the DNA segment of claim 6.

10. A host cell transformed with the vector of claim 7.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 2000 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycobacterium tuberculosis ( x i ) SEQUENCE DESCRIPTION: SEQ ID NO:1:

```
TGGTGGGGAT  GGCACGGCGC  CGGCTGGTTT  TTGTTGACGC  TGATGGTGCT            50

GACGCTCTGC  ATAGGCGTCC  CACCGATCGC  CGGCCCGGTC  ATGGCGCCGT           100

GAGCCGTCGG  CCAGGTCGGC  CGCGGTCAAC  AAATAAATGG  GTCAGATCCC           150

TCCACAACCC  GTTCGACGAG  TTCTACCGTT  GATGGTAGTG  CCTGGTAATG           200

GGCAGAAATG  GCGGAATAGG  ACGGAAACGG  AGGAGGCCAT  GGGCGACACC           250

TATCGTGACC  CCGTCGACCA  CTTGCGGACG  ACGCGGCCGC  TTGCCGGCGA           300

GTCGCTGATC  GACGTGGTGC  ATTGGCCTGG  GTATCTGTTG  ATTGTGGCCG           350

GTGTCGTCGG  CGGCGTCGGA  GCTCTTGCGG  CTTTCGGCAC  CGGACATCAC           400

GCCGAGGGCA  TGACCTTTGG  TGTGGTGGCG  ATTGTCGTCA  CAGTGGTTGG           450

TTTGGCGTGG  CTAGCGTTCG  AGCATCGGCG  GATACGCAAG  ATTGCCGATC           500
```

-continued

| | | | | |
|---|---|---|---|---|
| GCTGGTATAC | CGAACATCCC | GAAGTCCGGC | GGCAGCGGCT | GGCCGGCTAG | 550 |
| ACATCCTAGT | GCGGCTGGAA | ATCCCGGCAT | CGCGGGGTTT | CACCGGCAGC | 600 |
| TGCGAATGGG | TATCACGGGT | ACACCATGAT | GAATCCCGAC | CATGTTGCGT | 650 |
| TAGATCCCCA | CTACCAGCAG | GTCCGACCAT | GACCGACCAG | CTCGAAGACC | 700 |
| AGACCCAAGG | CGGGAGTACT | GTCGATCGAA | GCTTGCCGGG | AGGGTGCATG | 750 |
| GCCGACTCGG | ATTTACCCAC | CAAGGGGCGC | CAACGCGGTG | TCCGCGCCGT | 800 |
| CGAGCTGAAC | GTTGCTGCCC | GCCTGGAGAA | CCTGGCGCTG | CTGCGCACCC | 850 |
| TGGTCGGCGC | CATCGGCACC | TTCGAGGACC | TGGATTTCGA | CGCCGTGGCC | 900 |
| GACCTGAGGT | TGGCGGTGGA | CGAGGTGTGC | ACCCGGTTGA | TTCGCTCGGC | 950 |
| CTTGCCGGAT | GCCACCCTGC | GCCTGGTGGT | CGATCCNCGA | AAAGACGAAG | 1000 |
| TTGTGGTGGA | GGCTTCTGCT | GCCTGCGACA | CCCACGACGT | GGTGGCACCG | 1050 |
| GGCAGCTTTA | GCTGGCATGT | CCTGACCGCG | CTGGCCGACG | ACGTCCAGAC | 1100 |
| CTTCCACGAC | GGTCGCCAGC | CCGATGTAGC | CGGCAGTGTC | TTCGGCATCA | 1150 |
| CGTTGACCGC | CCGACGGGCG | GCATCCAGCA | GGTGACGGCG | CGCGCTGCCG | 1200 |
| GCGGTTCTGC | ATCGCGAGCT | AACGAATACG | CCGACGTTCC | GGAGATGTTT | 1250 |
| CGCGAGCTGG | TTGGTTTGCC | TGCCGGCTCA | CCGGAATTCC | AGCGGCACCG | 1300 |
| GGACAAGATC | GTTCAGCGGT | GCTTGCCGCT | GGCCGATCAC | ATCGCGCGGC | 1350 |
| GGTTCGAGGG | TCGCGGCGAA | CCGCGTGACG | ACCTTATTCA | GGTCGCGCGG | 1400 |
| GTCGGGCTGG | TCAACGCCGC | GGTTCGCTTC | GACGTGAAGA | CCGGGTCGGA | 1450 |
| CTTCGTCTCC | TTCGCGGTTC | CTACCATCAT | GGGCGAGGTC | CGACGACACT | 1500 |
| TCCGCGACAA | CAGCTGGTCG | GTCAAGGTTC | CCCGGCGTCT | CAAGGAACTG | 1550 |
| CATCTGCGGC | TAGGTACCGC | CACCGCCGAT | TTGTCGCAGC | GGCTCGGGCG | 1600 |
| GGCGCCGTCG | GCATCGGAGC | TCGCCGCGGA | GCTCGGGATG | GACCGCGCTG | 1650 |
| AGGTTATCGA | AGGTTTGCTG | GCGGGTAGTT | CCTACCACAC | CTTGTCCATC | 1700 |
| GACAGCGGTG | GCGGCAGCGA | CGACGATGCC | CGCGCAATCA | CAGACACCCT | 1750 |
| GGGCGACGTG | GATGCGGGTC | TTGACCAGAT | CGAGAATCGG | GAGGTGCTTC | 1800 |
| GTCCGTTGCT | CGAGGCGTTG | SCCGAGCGGG | AACGAACGGT | CTTGGTGCTC | 1850 |
| AGGTTCTTCG | ACTCGATGAC | CCAAACGCAG | ATCGCCGAGC | GCGTCGGTAT | 1900 |
| CTCACAGATG | CACGTGTCGC | GGGTGCTGGC | CAAGTCATTG | GCACGGCTAC | 1950 |
| GGGATCAGTT | GGAGTAGCCG | CCGGGCTTAC | TTGGATCTCG | GCGRAGCACC | 2000 |

(2) INFORMATION FOR SEQ ID NO:2:

(i) SEQUENCE CHARACTERISTICS:
        (A) LENGTH: 261 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Mycobacterium tuberculosis (xi) SEQUENCE DESCRIPTION: SEQ ID NO:2:

| Met | Thr | Ala | Arg | Ala | Ala | Gly | Gly | Ser | Ala | Ser | Arg | Ala | Asn | Glu | Tyr |
|---|---|---|---|---|---|---|---|---|---|---|---|---|---|---|---|
| 1 | | | | 5 | | | | | 10 | | | | | 15 | |

-continued

| | | | | | | | | | | | | | | |
|---|---|---|---|---|---|---|---|---|---|---|---|---|---|---|
| Ala | Asp | Val | Pro<br>20 | Glu | Met | Phe | Arg<br>25 | Glu | Leu | Val | Gly | Leu<br>30 | Pro | Ala | Gly |
| Ser | Pro | Glu<br>35 | Phe | Gln | Arg | His | Arg<br>40 | Asp | Lys | Ile | Val | Gln<br>45 | Arg | Cys | Leu |
| Pro | Leu<br>50 | Ala | Asp | His | Ile | Ala<br>55 | Arg | Arg | Phe | Glu | Gly<br>60 | Arg | Gly | Glu | Pro |
| Arg<br>65 | Asp | Asp | Leu | Ile | Gln<br>70 | Val | Ala | Arg | Val | Gly<br>75 | Leu | Val | Asn | Ala | Ala<br>80 |
| Val | Arg | Phe | Asp | Val<br>85 | Lys | Thr | Gly | Ser | Asp<br>90 | Phe | Val | Ser | Phe | Ala<br>95 | Val |
| Pro | Thr | Ile | Met<br>100 | Gly | Glu | Val | Arg | Arg<br>105 | His | Phe | Arg | Asp | Asn<br>110 | Ser | Trp |
| Ser | Val | Lys<br>115 | Val | Pro | Arg | Arg | Leu<br>120 | Lys | Glu | Leu | His | Leu<br>125 | Arg | Leu | Gly |
| Thr | Ala<br>130 | Thr | Ala | Asp | Leu | Ser<br>135 | Gln | Arg | Leu | Gly | Arg<br>140 | Ala | Pro | Ser | Ala |
| Ser<br>145 | Glu | Leu | Ala | Ala | Glu<br>150 | Leu | Gly | Met | Asp | Arg<br>155 | Ala | Glu | Val | Ile | Glu<br>160 |
| Gly | Leu | Leu | Ala | Gly<br>165 | Ser | Ser | Tyr | His | Thr<br>170 | Leu | Ser | Ile | Asp | Ser<br>175 | Gly |
| Gly | Gly | Ser | Asp<br>180 | Asp | Asp | Ala | Arg | Ala<br>185 | Ile | Thr | Asp | Thr | Leu<br>190 | Gly | Asp |
| Val | Asp | Ala<br>195 | Gly | Leu | Asp | Gln | Ile<br>200 | Glu | Asn | Arg | Glu | Val<br>205 | Leu | Arg | Pro |
| Leu | Leu<br>210 | Glu | Ala | Leu | Pro | Glu<br>215 | Arg | Glu | Arg | Thr | Val<br>220 | Leu | Val | Leu | Arg |
| Phe<br>225 | Phe | Asp | Ser | Met | Thr<br>230 | Gln | Thr | Gln | Ile | Ala<br>235 | Glu | Arg | Val | Gly | Ile<br>240 |
| Ser | Gln | Met | His | Val<br>245 | Ser | Arg | Val | Leu | Ala<br>250 | Lys | Ser | Leu | Ala | Arg<br>255 | Leu |
| Arg | Asp | Gln | Leu<br>260 | Glu | | | | | | | | | | | |

( 2 ) INFORMATION FOR SEQ ID NO:3:

( i ) SEQUENCE CHARACTERISTICS:
        ( A ) LENGTH: 242 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Mycobacterium tuberculosis ( x i ) SEQUENCE DESCRIPTION: SEQ ID NO:3:

| | | | | | | | | | | | | | | |
|---|---|---|---|---|---|---|---|---|---|---|---|---|---|---|
| Met<br>1 | Ala | Ser | Val | Arg<br>5 | Ala | Ser | Ala | Asp | Thr<br>10 | Gln | Asp | Cys | Arg | Ser<br>15 | Leu |
| Val | Tyr | Arg | Thr<br>20 | Ser | Arg | Ser | Pro | Ala<br>25 | Ala | Ala | Ala | Gly | Arg<br>30 | Leu | Asp |
| Ile | Leu | Val<br>35 | Arg | Leu | Glu | Ile | Pro<br>40 | Ala | Ser | Arg | Gly | Phe<br>45 | Thr | Gly | Ser |
| Cys | Glu<br>50 | Trp | Val | Ser | Arg | Val<br>55 | His | His | Asp | Glu | Ser<br>60 | Arg | Pro | Cys | Cys |
| Val | Arg | Ser | Pro | Leu | Pro | Ala | Gly | Pro | Thr | Met | Thr | Asp | Gln | Leu | Glu |

```
                     65                              70                              75                              80
Asp  Gln  Thr  Gln  Gly  Gly  Ser  Thr  Val  Asp  Arg  Ser  Leu  Pro  Gly  Gly
                    85                              90                              95

Cys  Met  Ala  Asp  Ser  Asp  Leu  Pro  Thr  Lys  Gly  Arg  Gln  Arg  Gly  Val
                   100                             105                             110

Arg  Ala  Val  Glu  Leu  Asn  Val  Ala  Ala  Arg  Leu  Glu  Asn  Leu  Ala  Leu
                   115                             120                             125

Leu  Arg  Thr  Leu  Val  Gly  Ala  Ile  Gly  Thr  Phe  Glu  Asp  Leu  Asp  Phe
          130                             135                             140

Asp  Ala  Val  Ala  Asp  Leu  Arg  Leu  Ala  Val  Asp  Glu  Val  Cys  Thr  Arg
145                           150                             155                           160

Leu  Ile  Arg  Ser  Ala  Leu  Pro  Asp  Ala  Thr  Leu  Arg  Leu  Val  Val  Asp
                   165                             170                             175

Pro  Arg  Lys  Asp  Glu  Val  Val  Val  Glu  Ala  Ser  Ala  Ala  Cys  Asp  Thr
                   180                             185                             190

His  Asp  Val  Val  Ala  Pro  Gly  Ser  Phe  Ser  Trp  His  Val  Leu  Thr  Ala
                   195                             200                             205

Leu  Ala  Asp  Asp  Val  Gln  Thr  Phe  His  Asp  Gly  Arg  Gln  Pro  Asp  Val
          210                             215                             220

Ala  Gly  Ser  Val  Phe  Gly  Ile  Thr  Leu  Thr  Ala  Arg  Arg  Ala  Ala  Ser
225                                     230                             235                           240

Ser  Arg
```

( 2 ) INFORMATION FOR SEQ ID NO:4:

( i ) SEQUENCE CHARACTERISTICS:
        ( A ) LENGTH: 137 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Mycobacterium tuberculosis ( x i ) SEQUENCE DESCRIPTION: SEQ ID NO:4:

```
Met  Gly  Gln  Ile  Pro  Pro  Gln  Pro  Val  Arg  Arg  Val  Leu  Pro  Leu  Met
1                        5                              10                             15

Val  Val  Pro  Gly  Asn  Gly  Gln  Lys  Trp  Arg  Asn  Arg  Thr  Glu  Thr  Glu
                    20                              25                              30

Glu  Ala  Met  Gly  Asp  Thr  Tyr  Arg  Asp  Pro  Val  Asp  His  Leu  Arg  Thr
          35                              40                              45

Thr  Arg  Pro  Leu  Ala  Gly  Glu  Ser  Leu  Ile  Asp  Val  Val  His  Trp  Pro
     50                              55                              60

Gly  Tyr  Leu  Leu  Ile  Val  Ala  Gly  Val  Val  Gly  Val  Gly  Val  Ala  Leu
65                            70                              75                            80

Ala  Ala  Phe  Gly  Thr  Gly  His  His  Ala  Glu  Gly  Met  Thr  Phe  Gly  Val
                    85                              90                              95

Val  Ala  Ile  Val  Val  Thr  Val  Val  Gly  Leu  Ala  Trp  Leu  Ala  Phe  Glu
                   100                             105                             110

His  Arg  Arg  Ile  Arg  Lys  Ile  Ala  Asp  Arg  Trp  Tyr  Thr  Glu  His  Pro
                   115                             120                             125

Glu  Val  Arg  Arg  Gln  Arg  Leu  Ala  Gly
          130                             135
```

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mycobacterium tuberculosis ( x i ) SEQUENCE DESCRIPTION: SEQ ID NO:5:

AACCTGCGHC TSGTSGTC 18

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:6:

Asn Leu Arg Leu Val Val
1                    5

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mycobacterium tuberculosis ( x i ) SEQUENCE DESCRIPTION: SEQ ID NO:7:

CTGNCGKATC CACCASGTSG CRTA 24

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Mycobacterium tuberculosis ( x i ) SEQUENCE DESCRIPTION: SEQ ID NO:8:

Tyr Ala Thr Trp Trp Ile Arg Gln
1                    5

( 2 ) INFORMATION FOR SEQ ID NO:9:

( i ) SEQUENCE CHARACTERISTICS:
        ( A ) LENGTH: 287 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Streptomyces coelicolor ( x i ) SEQUENCE DESCRIPTION: SEQ ID NO:9:

```
Met  Pro  Ala  Ser  Thr  Ala  Pro  Gln  Ala  Pro  Ala  Pro  Pro  Ala  Gln
  1              5                   10                       15
Ala  Gln  Ala  Gln  Ala  Pro  Ala  Gln  Ala  Gln  Glu  Ala  Pro  Ala  Pro  Gln
              20                   25                       30
Arg  Ser  Arg  Gly  Ala  Asp  Thr  Arg  Ala  Leu  Thr  Gln  Val  Leu  Phe  Gly
              35                   40                       45
Glu  Leu  Lys  Gly  Leu  Ala  Pro  Gly  Thr  Pro  Glu  His  Asp  Arg  Val  Arg
      50                        55                   60
Ala  Ala  Leu  Ile  Glu  Ala  Asn  Leu  Pro  Leu  Val  Arg  Tyr  Ala  Ala  Ala
 65                        70                   75                        80
Arg  Phe  Arg  Ser  Arg  Asn  Glu  Pro  Met  Glu  Asp  Val  Val  Gln  Val  Gly
                   85                   90                        95
Thr  Ile  Gly  Leu  Ile  Asn  Ala  Ile  Asp  Arg  Phe  Asp  Pro  Glu  Arg  Gly
              100                       105                      110
Val  Gln  Phe  Pro  Thr  Phe  Ala  Met  Pro  Thr  Val  Val  Gly  Glu  Ile  Lys
              115                       120                      125
Arg  Tyr  Phe  Arg  Asp  Asn  Val  Arg  Thr  Val  His  Val  Pro  Arg  Arg  Leu
     130                        135                  140
His  Glu  Leu  Trp  Val  Gln  Val  Asn  Ser  Ala  Thr  Glu  Asp  Leu  Thr  Thr
145                             150                  155                      160
Ala  Phe  Gly  Arg  Ser  Pro  Thr  Thr  Ala  Glu  Ile  Ala  Glu  Arg  Leu  Arg
                   165                       170                      175
Ile  Thr  Glu  Glu  Glu  Val  Leu  Ser  Cys  Ile  Glu  Ala  Gly  Arg  Ser  Tyr
              180                       185                      190
His  Ala  Thr  Ser  Leu  Glu  Ala  Ala  Gln  Glu  Gly  Asp  Gly  Leu  Pro  Gly
          195                       200                  205
Leu  Leu  Asp  Arg  Leu  Gly  Tyr  Glu  Asp  Pro  Ala  Leu  Asp  Gly  Val  Glu
     210                       215                   220
His  Arg  Asp  Leu  Val  Arg  His  Leu  Leu  Val  Gln  Leu  Pro  Glu  Arg  Glu
225                         230                  235                           240
Gln  Arg  Ile  Leu  Leu  Leu  Arg  Tyr  Tyr  Ser  Asn  Leu  Thr  Gln  Ser  Gln
                        245                  250                       255
Ile  Ser  Ala  Glu  Leu  Gly  Val  Ser  Gln  Met  His  Val  Ser  Arg  Leu  Leu
               260                       265                      270
Ala  Arg  Ser  Phe  Gln  Arg  Leu  Arg  Ser  Ala  Asn  Arg  Ile  Asp  Ala
          275                       280                  285
```

( 2 ) INFORMATION FOR SEQ ID NO:10:

( i ) SEQUENCE CHARACTERISTICS:
        ( A ) LENGTH: 255 amino acids
        ( B ) TYPE: amino acid
        ( D ) TOPOLOGY: linear ( i i ) MOLECULE TYPE: protein (  i i i  ) HYPOTHETICAL: NO (  v i  ) ORIGINAL SOURCE:
    ( A ) ORGANISM: Bacillus subtilis (  x i  ) SEQUENCE DESCRIPTION: SEQ ID NO:10:

```
Met Asp Val Glu Val Lys Lys Asn Gly Lys Asn Ala Gln Leu Lys Asp
1               5                   10                  15
His Glu Val Lys Glu Leu Ile Lys Gln Ser Gln Asn Gly Asp Gln Gln
            20                  25                  30
Ala Arg Asp Leu Leu Ile Glu Lys Asn Met Arg Leu Val Trp Ser Val
        35                  40                  45
Val Gln Arg Phe Leu Asn Arg Gly Tyr Glu Pro Asp Asp Leu Phe Gln
    50                  55                  60
Ile Gly Cys Ile Gly Leu Leu Lys Ser Val Asp Lys Phe Asp Leu Thr
65                  70                  75                  80
Tyr Asp Val Arg Phe Ser Thr Tyr Ala Val Pro Met Ile Ile Gly Glu
                85                  90                  95
Ile Gln Arg Phe Ile Arg Asp Asp Gly Thr Val Lys Val Ser Arg Ser
            100                 105                 110
Leu Lys Glu Leu Gly Asn Lys Ile Arg Arg Ala Lys Asp Glu Leu Ser
        115                 120                 125
Lys Thr Leu Gly Arg Val Pro Thr Val Gln Glu Ile Ala Asp His Leu
    130                 135                 140
Glu Ile Glu Ala Glu Asp Val Val Leu Ala Gln Glu Ala Val Arg Ala
145                 150                 155                 160
Pro Ser Ser Ile His Glu Thr Val Tyr Glu Asn Asp Gly Asp Pro Ile
                165                 170                 175
Thr Leu Leu Asp Gln Ile Ala Asp Asn Ser Glu Glu Lys Trp Phe Asp
            180                 185                 190
Lys Ile Ala Leu Lys Glu Ala Ile Ser Asp Leu Glu Glu Arg Glu Lys
        195                 200                 205
Leu Ile Val Tyr Leu Arg Tyr Tyr Lys Asp Gln Thr Gln Ser Glu Val
    210                 215                 220
Ala Glu Arg Leu Gly Ile Ser Gln Val Gln Val Ser Arg Leu Glu Lys
225                 230                 235                 240
Lys Ile Leu Lys Gln Ile Lys Val Gln Met Asp His Thr Asp Gly
                245                 250                 255
```

( 2 ) INFORMATION FOR SEQ ID NO:11:

(  i  ) SEQUENCE CHARACTERISTICS:
        ( A ) LENGTH: 262 amino acids
        ( B ) TYPE: amino acid
        ( D ) TOPOLOGY: linear (  i i  ) MOLECULE TYPE: protein (  i i i  ) HYPOTHETICAL: NO (  v i  ) ORIGINAL SOURCE:
        ( A ) ORGANISM: Bacillus subtilis (  x i  ) SEQUENCE DESCRIPTION: SEQ ID NO:11:

```
Met Thr Gln Pro Ser Lys Thr Thr Lys Leu Thr Lys Asp Glu Val Asp
1               5                   10                  15
Arg Leu Ile Ser Asp Tyr Gln Thr Lys Gln Asp Glu Gln Ala Gln Glu
            20                  25                  30
Thr Leu Val Arg Val Tyr Thr Asn Leu Val Asp Met Leu Ala Lys Lys
        35                  40                  45
```

```
Tyr  Ser  Lys  Gly  Lys  Ser  Phe  His  Glu  Asp  Leu  Arg  Gln  Val  Gly  Met
     50                       55                      60

Ile  Gly  Leu  Leu  Gly  Ala  Ile  Lys  Arg  Tyr  Asp  Pro  Val  Val  Gly  Lys
65                       70                      75                           80

Ser  Phe  Glu  Ala  Phe  Ala  Ile  Pro  Thr  Ile  Ile  Gly  Glu  Ile  Lys  Arg
               85                      90                           95

Phe  Leu  Arg  Asp  Lys  Thr  Trp  Ser  Val  His  Val  Pro  Arg  Arg  Ile  Lys
               100                      105                      110

Glu  Leu  Gly  Pro  Arg  Ile  Lys  Met  Ala  Val  Asp  Gln  Leu  Thr  Thr  Glu
          115                      120                      125

Thr  Gln  Arg  Ser  Pro  Lys  Val  Glu  Glu  Ile  Ala  Glu  Phe  Leu  Asp  Val
     130                      135                      140

Ser  Glu  Glu  Glu  Val  Leu  Glu  Thr  Met  Glu  Met  Gly  Lys  Ser  Tyr  Gln
145                      150                      155                           160

Ala  Leu  Ser  Val  Asp  His  Ser  Ile  Glu  Ala  Asp  Ser  Asp  Gly  Ser  Thr
               165                      170                           175

Val  Thr  Ile  Leu  Asp  Ile  Val  Gly  Ser  Gln  Glu  Asp  Gly  Tyr  Glu  Arg
               180                 185                           190

Val  Asn  Gln  Gln  Leu  Met  Leu  Gln  Ser  Val  Leu  His  Val  Leu  Ser  Asp
          195                      200                      205

Arg  Glu  Lys  Gln  Ile  Ile  Asp  Leu  Thr  Tyr  Ile  Gln  Asn  Lys  Ser  Gln
     210                      215                      220

Lys  Glu  Thr  Gly  Asp  Ile  Leu  Gly  Ile  Ser  Gln  Met  His  Val  Ser  Arg
225                      230                      235                           240

Leu  Gln  Arg  Lys  Ala  Val  Lys  Lys  Leu  Arg  Glu  Ala  Leu  Ile  Glu  Asp
               245                      250                      255

Pro  Ser  Met  Glu  Leu  Met
               260
```